(12) United States Patent
Policicchio

(10) Patent No.: US 9,743,999 B2
(45) Date of Patent: Aug. 29, 2017

(54) DENTAL PROPHYLAXIS DEVICE AND AIR APPLIANCE

(71) Applicant: Piero A. Policicchio, Holland, MI (US)

(72) Inventor: Piero A. Policicchio, Holland, MI (US)

( * ) Notice: Subject to any disclaimer, the term of this patent is extended or adjusted under 35 U.S.C. 154(b) by 273 days.

(21) Appl. No.: 14/472,440

(22) Filed: Aug. 29, 2014

(65) Prior Publication Data

US 2016/0058526 A1 Mar. 3, 2016

(51) Int. Cl.
| | | |
|---|---|---|
| *A61C 1/00* | (2006.01) | |
| *A61C 3/025* | (2006.01) | |
| *A61C 17/02* | (2006.01) | |
| *A61C 1/08* | (2006.01) | |
| *A61N 5/06* | (2006.01) | |

(52) U.S. Cl.
CPC ............ *A61C 3/025* (2013.01); *A61C 1/0084* (2013.01); *A61C 1/088* (2013.01); *A61C 17/0202* (2013.01); *A61N 5/062* (2013.01); *A61N 5/0624* (2013.01); *A61C 17/0217* (2013.01); *A61N 2005/0606* (2013.01)

(58) Field of Classification Search
CPC ..... A61C 3/025; A61C 1/0084; A61C 1/0061; A61C 1/087; A61C 17/0202; A61C 17/0205; A61C 17/028; A61C 17/227
See application file for complete search history.

(56) References Cited

U.S. PATENT DOCUMENTS

| | | |
|---|---|---|
| 3,164,153 A | 1/1965 | Zorzi |
| 3,882,638 A | 5/1975 | Black |
| 3,971,136 A | 7/1976 | Madsen |
| 3,972,123 A | 8/1976 | Black |
| 4,111,193 A | 9/1978 | Jousson |
| 4,174,571 A | 11/1979 | Gallant |
| 4,214,871 A | 7/1980 | Arnold |
| 4,253,610 A | 3/1981 | Larkin |
| 4,412,402 A | 11/1983 | Gallant |
| 4,462,803 A | 7/1984 | Landgraf et al. |
| 4,540,365 A | 9/1985 | Nelson et al. |
| 4,776,794 A | 10/1988 | Meller |
| 4,903,688 A | 2/1990 | Bibby et al. |
| 4,906,187 A | 3/1990 | Amadera |
| 4,950,160 A | 8/1990 | Karst |
| 4,979,504 A | 12/1990 | Mills |
| 4,984,984 A | 1/1991 | Esrock |
| 5,094,615 A | 3/1992 | Bailey |
| 5,098,291 A | 3/1992 | Curtis et al. |
| 5,120,219 A | 6/1992 | De Farcy |
| 5,165,456 A | 11/1992 | Woolman |
| 5,186,625 A | 2/1993 | Bailey |
| 5,393,228 A | 2/1995 | Policicchio |

(Continued)

*Primary Examiner* — George Evanisko

(74) *Attorney, Agent, or Firm* — Harness, Dickey & Pierce, P.L.C.

(57) ABSTRACT

A dental prophylaxis and air appliance having a pressurized air source, a hand piece, and a manually actuated slurry container containing a mixture of dry or wetted abrasive and non-abrasive components. The compressed air is delivered to the hand piece by a line that combines the compressed air with the components and discharges the post-mixed water slurry of abrasive or non-abrasive components. The hand piece is configured to include a series of valves adapted to define one or more stages for containing components and encourage mixing thereof during operation.

19 Claims, 2 Drawing Sheets

(56) References Cited

U.S. PATENT DOCUMENTS

| | | | |
|---|---|---|---|
| 5,934,904 A | 8/1999 | Elrod et al. | |
| 5,941,702 A | 8/1999 | Sharp et al. | |
| 6,093,021 A | 7/2000 | Rainey | |
| 6,120,755 A | 9/2000 | Jacobs | |
| 6,155,824 A * | 12/2000 | Kamen | A61C 17/0208 433/80 |
| 6,287,180 B1 | 9/2001 | Hertz | |
| 6,416,321 B2 | 7/2002 | Gugel et al. | |
| 6,439,966 B2 | 8/2002 | Bruns et al. | |
| 6,485,303 B1 | 11/2002 | Goldman et al. | |
| 6,485,304 B2 | 11/2002 | Beerstecher et al. | |
| 6,497,572 B2 | 12/2002 | Hood et al. | |
| 6,508,648 B2 | 1/2003 | Aumuller et al. | |
| 6,527,551 B2 * | 3/2003 | Lanfranchi | A61C 1/0084 433/77 |
| 6,755,650 B2 * | 6/2004 | Decosterd | A61C 1/0084 222/185.1 |
| 2006/0078844 A1 * | 4/2006 | Goldman | A61C 1/0084 433/80 |
| 2007/0041779 A1 * | 2/2007 | Kuo | A46B 11/0058 401/188 R |

* cited by examiner

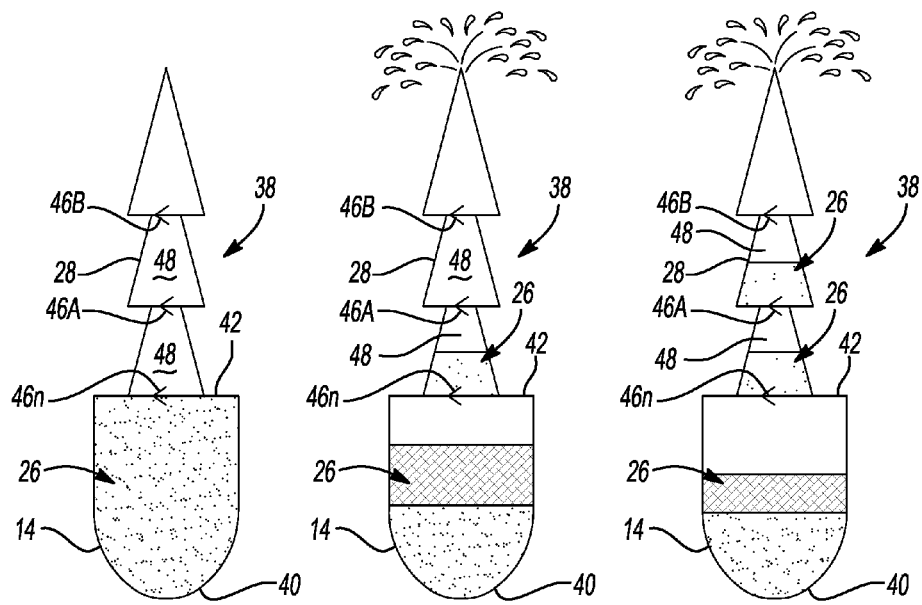
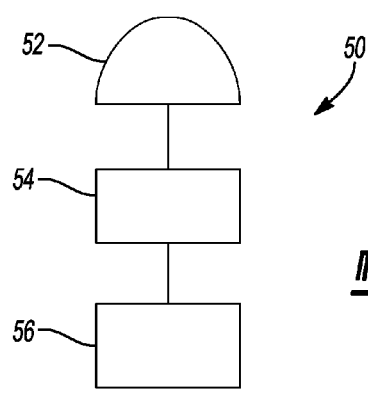

DENTAL PROPHYLAXIS DEVICE AND AIR APPLIANCE

FIELD

The present disclosure relates to a dental prophylaxis device for home use and, more particularly, relates to a dental prophylaxis device that is particularly suited for cleaning and providing prophylaxis of teeth, gingiva, and other oral tissue.

BACKGROUND

This section provides background information related to the present disclosure which is not necessarily prior art.

Over the years, numerous dental devices have been proposed which provide prophylaxis through what is commonly referred to as a "sandblasting" technique. While sometimes intended for home use, these devices are more often only appropriate for office or clinical use because of the additional equipment needed for their operation. This equipment is both complex and expensive.

One of the first devices of the above-mentioned type is disclosed in U.S. Pat. No. 3,972,123. The device of the '123 patent discloses a nozzle which ejects an abrasive laden air stream surrounded by a shroud of warm water. Improving on the '123 patent is U.S. Pat. No. 4,174,571. The '571 patent discloses the use of a water-soluble abrasive in the air stream. Unfortunately, both of these systems are quite elaborate and therefore costly to produce, manufacture, purchase, and maintain, all of which make them not particularly suited for home use.

One general problem with these particular types of devices is that the nozzle of the devices is susceptible to becoming clogged by the abrasive in the air stream and therefore requires frequent maintenance. This problem has led to the development of numerous devices, which utilize some variety of mechanism for agitating of the abrasive material in an attempt to prevent the discharge ports from becoming clogged. For obvious reasons, a device, which is not susceptible to clogging without the added expense of an agitating mechanism, is desirable.

U.S. Pat. No. 4,214,871 discloses the introduction of a soluble abrasive particle into the liquid stream, which is discharged against the teeth and gingiva. In this device, water, at household pressures, is delivered through a nozzle that entrains the abrasive particles into the liquid stream (where they partially dissolve) and ejects them against the teeth and the adjacent oral tissues. Household water pressure, however, has proven to be ineffective at providing sufficient pressures for adequately removing plaque and other calculus. A greater force for propelling the liquid entrained particles is needed.

U.S. Pat. No. 4,776,794 uses a piston applying pressure to push pre-mixed abrasive liquid into an air stream. The device uses a water pipe and a mixing chamber at the tip to incorporate air, water, and premixed slurry. The device was designed for a professional setting and is not readily adaptable for home use since it requires a separate pressurized air source and pre-mixed abrasive slurry. The premixed slurry does not allow additional medicaments to be added by user.

U.S. Pat. Application No. 2003/0013063 discloses a container holding pre-mixed slurry. A bubble foam laden with abrasive particles is forced into a jet stream of air similar to U.S. Pat. No. 5,203,698. A drawback to this appliance is that it uses pre-mixed slurry, which decreases the shelf life of product. In addition, the system is complex and difficult to manufacture.

U.S. Pat. No. 5,393,228 employs a system of air, water, and dental cleaner to clean teeth and around gums, whereby air pressurizes a water chamber, which in turn uses water to pressurize a receptacle of dental cleaner forcing the wetted cleaner into a stream of accelerated air flow.

As can be seen from the above discussion, the principal direction of technology in this field has been toward devices, which are better suited for use in the professional dental office where the costs of the equipment necessary for providing compressed air and water are more easily afforded and recovered. Additionally, the prior devices are cumbersome since they require the use of specially prepared abrasives, such as finely milled sodium bicarbonate, an air/powder, or water/powder suspension.

SUMMARY

This section provides a general summary of the disclosure, and is not a comprehensive disclosure of its full scope or all of its features.

With the limitations of the prior art in mind, it is a principal object of the present invention to provide a dental prophylaxis device which is particularly suited to use in the home of a patient for daily and thorough lavage of the teeth, gingival tissue, and general oral cavity. However, it is also an object of the present invention to provide an air appliance, which is adaptable to alternative uses within the home, including uses unrelated to oral hygiene. The present invention could be used, for example, to operate various other household items, which perform scrubbing, spraying, dispensing, foaming, pumping, or other functions.

The air appliance of the present invention can be used for dermatological applications, recreational applications, toys, propulsion devices, preservation devices, marinating devices, drain opener, fire extinguisher, lather-maker, pressurized cooking devices, nasal and sinus cleansing applications, humidifying device, nebulizing devices, atomizing devices, manicuring applications, massaging device, air delivering tool devices, and painting devices.

The air appliance of the present invention uses a cleaning technique that directs an abrasive-laden fluid stream at the teeth, gingiva, and other oral tissue. The abrasive stream cleans out food particles while removing plaque from the surfaces of the teeth and at the tooth/gingiva interface. Additionally, the devices stimulate circulation in the gingiva and oxygenates various anaerobic bacteria, both of which help to prevent periodontal diseases.

An advantage to the present invention as a home device is the lack of a need for a pressurized water vessel. Another advantage is the user in the home can vary the dilution of the slurry and consequently the level of abrasiveness or efficacy of the cleaning, through the amount of water or other liquid used in wetting the dry components.

Additional benefits and advantages of the present invention will become apparent to those skilled in the art to which this invention relates from the subsequent description of the preferred embodiments and the appended claims, taken in conjunction with the accompanying drawings.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIGS. 3A-3C is a series of diagrammatic illustrations showing the progression of slurry along a series of stages according to the present teachings; and FIG. 4 is a diagrammatic illustration of a light activation system according to the present teachings.

Corresponding reference numerals indicate corresponding parts throughout the several views of the drawings.

DETAILED DESCRIPTION

Figure 1:
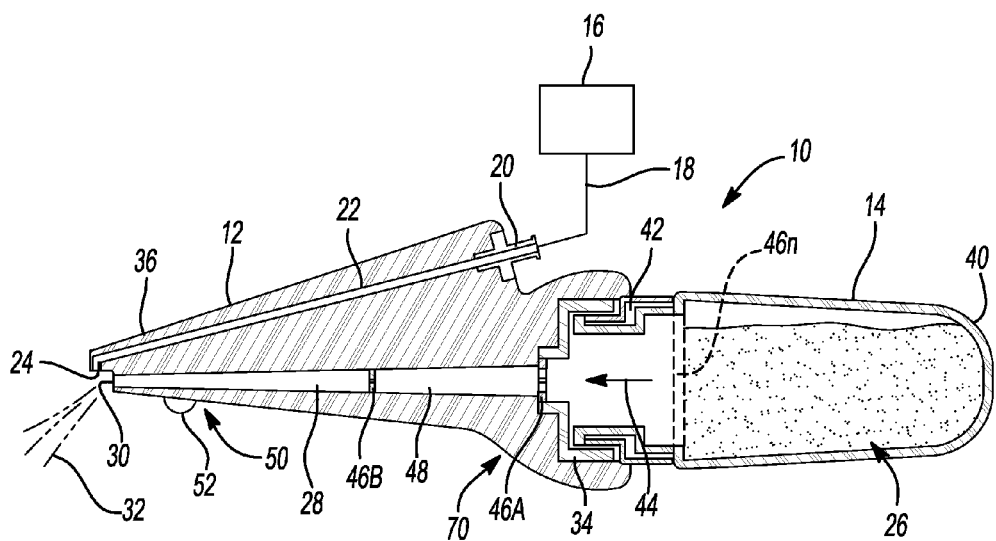
FIG. 1 is a diagrammatic illustration of an air appliance according to the principles of the present teachings.
Figure 2:
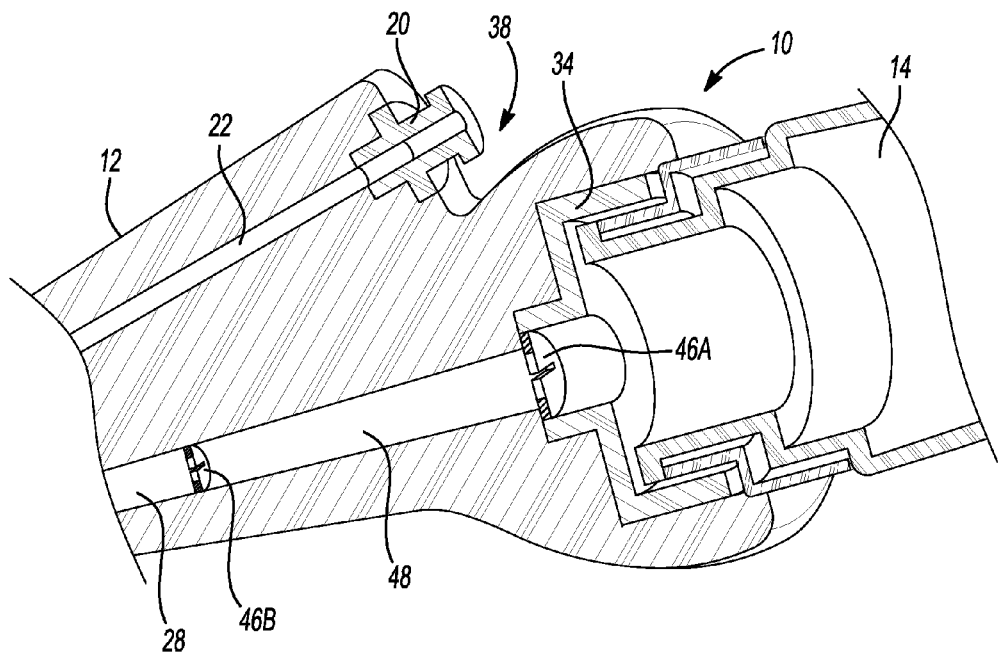
FIG. 2 is an enlarged cross-sectional perspective view illustrating the air appliance of the present teachings.

Example embodiments will now be described more fully with reference to the accompanying drawings.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The dental prophylaxis and air appliance of the present invention uses a cleaning technique that directs an abrasive-laden fluid stream at the teeth, gingiva, and other oral tissue. The abrasive stream cleans out food particles while removing plaque from the surfaces of the teeth and at the tooth/gingiva interface. Additionally, the devices stimulate circulation in the gingiva and oxygenates various anaerobic bacteria, both of which help to prevent and/or treat periodontal diseases.

Moreover, it should be appreciated that the present teachings provide a device that prevents and/or treats inflammation and infection of the surrounding tissue of teeth, periodontal disease being the most prevalent of all inflammatory diseases and one that exacerbates all other inflammatory diseases, and it should be understood that it can be used as an adjunct in the treatment other inflammatory diseases, such as, but not limited to, diabetes, heart disease, strokes, arthritis, vascular diseases, breast cancer, lung cancer, pancreatic cancer, kidney cancer, colon cancer and other cancers of inflammatory etiology, Alzheimer's and other dementias, prenatal care and preeclampsia, and erectile dysfunction, and can also be used in the treatment of blood markers of inflammation, such as, but not limited to, mmp, crp, Ip-pla2, il-1, il-6, periostin, and others known to those skilled in the art and also those yet to be identified. It should finally be understood that the present teachings can be used in the treatment of depression, peri-implantitis, and the like.

With reference to FIG. 1, a dental prophylaxis and air appliance (hereinafter "air appliance"), generally indicated at reference numeral 10, is provided according to the principles of the present invention. Air appliance 10 generally includes a hand piece 12, a slurry container 14 coupled to hand piece 12, and a compressed air source 16 in fluid communication with hand piece 12, which will be more fully described below. In some embodiments, compressed air source 16 comprises a power supply cord and actuation system such as that set forth in U.S. Patent Publication No. 2004-0202980, which is incorporated herein by reference.

A compressed air line 18 is coupled to hand piece 12 via a quick disconnect coupling member 20. Compressed air can be selectively introduced by an operator through compressed air line 18 and quick disconnect coupling member 20 into an air delivery tube 22 extending through hand piece 12 to a distal tip of hand piece 12. Specifically, air delivery tube 22 can terminate at a small bore orifice 24 in the tip of hand piece 12. In some embodiments, small bore orifice 24 can define an orifice diameter between about 0.20" and 0.45"; however, it should be understood that this diameter range can include alternative dimensions suitable for a particular application. In some embodiments, small bore orifice 24 is made of a resilient material, such as silicone, that is capable of providing a flexural response. This flexural response permits small bore orifice 24 to maintain a predetermined diameter, however, in response to a clog or other debris being present in air delivery tube 22, small bore orifice 24 can flex to a greater diameter to permit passage or expulsion of such debris material thereby preventing a clog. The flexural response characteristics can be selected by one skilled in the art through selection of the durometer of the material and the thickness of the material of the perimeter of small bore orifice 24. Small bore orifice 24 can be constructed during the molding process through the introduction of a cone-shaped slide pin or seat disposed in the mold.

In some embodiments, hand piece 12 can include a spray tip member 36 coupled thereto or formed integrally therewith. To this end, spray tip member 36 may have any one of a plurality of shapes, delivery streams, and applications. By way of non-limiting example, removable spray tip member 36 may include a brush, a sponge or rubber scraper, a tongue scraper, a periodontal aid, an upper and lower tray with multiple jets to deliver medium across all teeth simultaneously, or a pneumatic driving power brush system with air/slurry spray. In embodiments having a removable spray tip member 36, spray tip member 36 can be a quick change type having a 360° rotating individual user tip that can take on different shapes depending upon the embodiment. It should be understood that hand piece 12 and spray tip member 36 may be one self-contained disposable unit or an assembled unit.

It should be understood that slurry container 14 is removably mounted to hand piece 12 using any one of a number of conventional mounting device, such as, but not limited to, a snap-on fit, interference fit, locking engagement, slidable engagement, screwing connection, and the like. Preferably, a seal 34 is provided between slurry container 14 and hand piece 12 to prevent leakage. However, it is also important to understand that slurry container 14 may form any one of a number of shapes, such as those that naturally fit an operator's hand, encourages convenient loading (e.g. alternative loading ports), or extend in a direction other than generally axially aligned with hand piece 12. Additionally, it should be understood that slurry container 14 may be disposable to facilitate its use with a wide variety of materials.

In some embodiments, slurry container 14 and/or hand piece 12 can comprise a slurry delivery tube 28 fluidly coupling slurry container 14 to a slurry orifice 30 to deliver a slurry mixture 26 thereto. Slurry orifice 30 and small bore orifice 24 are disposed adjacent to each other such that a combination of slurry mixture 26 from slurry orifice 30 and compressed air from small bore orifice 24 combine at a predetermine delivery rate to form an atomized slurry and air spray 32. This delivery rate may be adjusted depending upon slurry consistency, slurry type, desired flow rate, operator application rate (as will be described herein) and the like. It should be appreciated that although slurry mixture 26 is presently described as being a liquid mixture, the present invention should not be regarded as being limited to such. A more complete description of alternative agents, materials, and the like that may be used in place of slurry mixture 26 is provide below.

Depending on the specific composition of slurry mixture 26, it has been found that in some applications the constituents of slurry mixture 26 can separate from solution to a combination of supernate (liquid) and precipitate (solid particles). The precipitate can often settle to a lower location in the storage vessel that can result in an inconsistent slurry composition. The inconsistent slurry can lead to reduced uniformity of slurry and air spray 32 and, thus, a reduction in cleaning performance. The inconsistent slurry composition can be cured through mixing of the slurry mixture 26 by an operator immediately before use. However, in situations where an operator fails to thoroughly mix slurry mixture 26 prior to use or a slurry mixture quickly separates, the present teachings provide an apparatus and method for overcoming such and thus conveying a properly mixed slurry mixture 26 to slurry orifice 30.

To this end, in some embodiments, slurry container 14 and slurry delivery system 54 can be configured to include several features that cooperate to form a fish ladder or weir-type, progressive dispensing system 38 that conveys and simultaneously ensures proper mixture of the slurry mixture 26. Dispensing system 38 can comprise a number of features that can be used singly or in combination to provide several advantages. In some embodiments, dispensing system 38 can start with a manually-compressible slurry container 14. In this way, manually-compressible slurry container 14 can be made of a resilient material, such as rubber, that is biased in an uncompressed position and compressible by the hand of an operator into a compressed position to mix slurry mixture 26 and further urge slurry mixture 26 into slurry delivery tube 28. In some embodiments, slurry container 14 can comprise a proximal end 40 and a distal end 42. Proximal end 40 can be formed of the aforementioned resilient material, while distal end 42 can be formed of a similar resilient material or other material. As discussed herein, distal end 42 can comprise a feature(s), such as threads, for selectively coupling slurry container 14 to hand piece 12. Slurry container 14 can be bulbous shaped to permit convenient manual actuation; however, it should be understood, that alternative shapes are possible.

In some embodiments, an interior volume of slurry container 14 is fluidly coupled with slurry delivery tube 28 to permit the flow of slurry mixture 26 therethrough and define a slurry pathway 44—the slurry pathway 44 extending from an interior volume of slurry container 14, along slurry delivery tube 28, and out slurry orifice 30. Dispensing system 38 can further comprise a plurality of weir gates or one-way valves 46 (46A, 46B, 46n) extending along the slurry pathway 44. One-way valves 46 act as check valves permitting flow of slurry mixture 26 or its individual constituents in a downstream direction along slurry pathway 44 and further generally preventing flow of slurry mixture 26 or its individual constituents in an upstream direction. One-way valves 46 are spaced along slurry pathway 44 to form a series of weirs or slurry compartments 48 containing a volume of slurry mixture 26 between adjacent one-way valves 46. It should be understood that any number of one-way valves 46 can be used in order to form a plurality of stages, as will be discussed herein. In some embodiments, one-way valve 46n can be disposed within a portion of slurry container 14 to serve as an initial one-way valve and further prevent spillage when installing slurry container 14 on hand piece 12.

Each of the plurality of one-way valves 46 can be configured as flapper valves being made of a suitable, resilient materials having a central aperture capable of opening in response to upstream pressure and automatically closing, based on their inherent resilient biasing force, once the upstream pressure is removed. In this way, one-way valves 46 can operate in response to manual actuation of slurry container 14 by an operator, which causes a rise in the internal pressure within slurry container 14 due to the reduced volume, that results in slurry mixture 26 being forced through one-way valve 46A against the biasing closing force of one-way valve 46A into slurry delivery tube 28. Once past one-way valve 46A, slurry mixture 26 can continue to flow along slurry pathway 44 to one-way valve 46B. Provided sufficient pressure exists in the slurry mixture 26 upstream of one-way valve 46B, slurry mixture 26 is forced through one-way valve 46B against the biasing closing force of one-way valve 46B further along slurry delivery tube 28 eventually exiting at slurry orifice 30. In some embodiments, slurry delivery tube 28 can taper from an upstream position to a downstream position to encourage an increase in dispensing rate and/or velocity.

Once actuation pressure is removed from slurry container 14, which causes a reduction in the internal pressure within slurry container 14 due to the increased volume, one-way valves 46 (e.g. 46A, 46B, 46n) automatically close in response to their inherent resilient biasing force. Such closure of one-way valves 46 traps a portion of slurry mixture 26 within a volume or stage of slurry pathway 44 between adjacent one-way valves 46, thereby preventing the return of slurry mixture 26 to slurry container 14. In this way, as illustrated in FIGS. 3A-3C, a portion of slurry mixture 26 is contained at a plurality of mixing stages 48 along slurry pathway 44. Each of the plurality of mixing stages 48, whose number is determined by the number of one-way valves 46, can act as a series of weirs or fish ladders that trap a portion of slurry mixture 26 along slurry pathway 44 and prevent precipitate from settling back into slurry container 14. If an operator fails to shake or otherwise mix slurry mixture 26 thoroughly (e.g. allowing slurry mixture 26 to separate into the aforementioned combination of air, supernate, and precipitate), the structure of the present teachings results in the slurry mixture 26 being stirred, agitated, or otherwise mixed by the introduction of slurry mixture 26 components from upstream being urged along slurry pathway 44 by manual actuation of slurry container 14. In other words, with portions of slurry mixture 26 being contained at each stage 48 along slurry pathway 44, manual actuation of slurry container 14 causes at least air and supernate to be urged into the next downstream stage (e.g. previously capture and staged slurry components) through one-way valve 46 causing precipitate and supernate contained in this next downstream stage to be stirred, agitated, or otherwise mixed. This mixture is then urged along slurry pathway 44 to a subsequent stage, again stirring, agitating, or otherwise mixing components in the next stage. Therefore, slurry mixture 26 is automatically mixed at or along mixing stages 48 due to the stage or weir configuration of the present teachings. Moreover, due to the thorough mixing of slurry mixture 26 along mixing stages 48, any propensity to clog is reduced.

In some embodiments, hydrophobic coatings or materials having inherent hydrophobic properties can be used to facilitate conveyance and/or application of slurry mixture 26. In this way, slurry container 14, slurry delivery tube 28, one-way valves 46, and/or other components of air appliance 10 can be hydrophobic.

The force produced by atomized slurry and air spray 32 is sufficient to remove food particles, plaque, tarter, and other dental calculus from the surfaces of the teeth, the areas between the teeth, and the tooth/gingiva interface. Additionally, the air and slurry stimulates circulation in the gingival tissues and oxygenates various anaerobic bacteria thereby inhibiting periodontal diseases. Using baking soda as the abrasive slurry also has the further effect of neutralizing the specific environment in which both the aerobic and anaerobic bacteria thrive.

As described above, slurry mixture 26 should not be interpreted as being limited to liquid slurries. As such, any one of a number of material components may be used and are anticipated as being within the scope of the present invention. By way of non-limiting example, air appliance 10 of the present invention may be used in connection with dry materials, premixed slurries, compressed tablets, or even premixed packets or dosages. Additionally, these materials may be used in any one of a number of forms, such as dry, gel, cream, fluid, or colloid suspension. Still further, the actual material used for cleansing and/or treatment may be chosen from at least the following: an abrasive (calcium triphosphate, psylumm husk, etc.), a non-abrasive, an anionic surfactant, a cationic surfactant, a nonionic surfactant, a medicament, a flavoring (mint, fruit, etc.), an astringent (tea tree oil, thymol, etc.), a disinfectant (chloride or chlorite ion, silver compound, sodium chloride, sodium bromide, sodium iodide, potassium chloride, potassium bromide, potassium iodide, magnesium chloride, magnesium bromide, magnesium iodide, calcium chloride, calcium bromide, calcium iodide, etc.), an oxygenating agent (hydrogen peroxide), an enzyme or a coenzyme (papaya extract, coenzyme Q10), a vitamin (alpha-tocopherol (vitamin E), pyridoxal (vitamin B6), ascorbic acid (vitamin C), vitamin B12, vitamin A, vitamin D, vitamin K, etc.), a mineral (zinc, calcium chloride, etc.), an organic, an inorganic, a sweetener (xylitol, saccharin, carrigin, etc.), a combatant, an antimicrobial (chlorhexidine gluconate, triclosan, etc.), an antibiotic (tetracycline, metrodizole, etc.), a bacteria, a virus, an antiviral agent (acyclovir, etc.), a desensitizing agent (potassium nitrate, acidic oxalate composition, fluoride, etc.), an odor-eating agent (zinc, sodium bicarbonate, etc.), an acid, a base, a neutral, a bleaching agent (carbamide peroxide), an antioxidant, an anti-inflammatory agent (salicylic acid, 4-amino salicylic acid, esters of salicylic acid, esters of 4-aminosalicylic acid, sulfanilamide, etc.), a sealant (waxes, poly-n-vinyl pyrrolidone, crystalline fatty alcohols, paraffins, polyethylene oxides, hydroxypropyl cellulose, and cellulose derivatives, etc.), a coating (glycerin, sorbitol, polyethylene glycol, polyglycerols, propylene glycol, etc.), an anti-tarter agent, an anti-adherent agent, an anti-agglomerate, a remineralization agent (fluoride, calcium, phosphate, etc.), a resorbable polymer (poly(D,L-lactide), poly(D,L-lactide-co-trimethylene carbonate), poly(ethylene-co-propylene), poly(ethylene-co-vinyl acetate), poly(D,L-lactide-co-glycolide), carboxymethylelhyl cellulose, synthetic hydroxyl functional polymers, polyacrylamide, polyoxymethylene, etc.), a copolymer, an astringent (grape seed extract, etc.), a disinfectant (chloride, chlorite ion, etc.), a time-releasing agent (hydroxyethylcellulose, selenium, etc.), a cox1 inhibitor, a cox2 inhibitor, a lipid, a protein, a carbohydrate, an oil alcohol, a phenol agent, a phosphorylated nucleotide (adenosine triphosphate (ADP), adenosine diphosphate (ADP), adenosine monophosphate (AMP), guanosine triphosphate (GTP), uridine triphosphate (UJTP), etc.), an amino acid (aspartic acid, glutamic acid, glutamine, arginine, glycine, etc.), an antihistamine (benadryl), a steroid (predonsone, prednisolone, prednisone, dexycorticosterone, cortisone, hydrocortisone, estrogen, etc.), a disintegrin (monoclonal antibodies, etc.), a glycosaminoglycan (hyaluronic acid, chondroitin sulfate, heparin, heparin sulfate, keratin sulfate, etc.), a growth factor (fibroblast growth factor (FGF), platelet-derived growth factor (PDGF), insulin-like growth factor (IGF), transforming growth factor (TGR), epidermal growth factor (EGF), etc.), a periodontal tissue regenerator (collagen, glycosaminoglycans (e.g., hyaluronic acid, heparin sulfate, chondroitin sulfate) proteoglycans (e.g., versican, biglycan), substrate adhesion molecules (e.g., fibronectin, vitronectin, laminin) etc.), an a hydrophobic layer (silicone oils, modified silicones, etc.).

Moreover, in some embodiments, air appliance 10 can comprise a light activation system 50 for use in activating a dye contained in slurry mixture 26. In some embodiments, as illustrated in FIGS. 1 and 4, light activation system 50 can comprise a light unit 52, a light control system 54, and a power source 56. Light activation system 50 is configured to cooperate with a dye contained in slurry mixture 26. The dye is ideally light activated such that the dye can be introduced as part of slurry and air spray 32 into the mouth of a patient or user, such as below the gum line into the periodontal crevasse. This dye can then be simultaneously activated by the presence of light activation system 50 so that the combination of light and dye are absorbed by microbes to disinfect the mouth. In some embodiments, the dye is a methylene blue dye, or other dye or medicaments or light activated medicaments known to those skilled in the art. Accordingly, the wavelength of light emitted from light unit 52 is selected to activate the particular dye being used. Light control system 54 can be a switch system that permits the independent actuation of light unit 52. However, it should be understood that light unit 52 can be automatically tied to use of air appliance 10 such that during any use of air appliance 10, light unit 52 is illuminated. Accordingly, the present teachings provide a mean to not only provide an abrasive cleaner (e.g. slurry mixture 26), but also to penetrate the biofilm and access the site and microbes for efficacy to occur. Moreover, the present teachings provide a jet propulsion-like system to deliver such dye during treatment, which is much improved compared to swishing or cannula irrigation without an abrasive component to penetrate the biofilm. This permits the molecules of the dye to contact the microbes for a higher kill rate. Although it should be understood that in some aspects, light unit 52 may be used for visual illumination of the area, its primary purpose is for activation of the associated dye within slurry and air spray 32 or slurry mixture 26.

Additionally, air appliance 10 of the present invention may also be adapted for both professional and home applications. Furthermore, air appliance 10 may be adapted to provide high, medium, low, or no (0) pressures depending upon the needs of the particular application. Still further, air appliance 10 may include an optional air tank ballast (not shown) in conjunction with the current design to provide an increase volume of air over a period of time, a super charger or volumetric reservoir of air. Additionally, other fluid bottles for other components or liquids may be used in conjunction with the present invention.

It should be appreciated from the foregoing that air appliance 10 of the present invention may also be used for dermatological applications, recreational applications, toys, propulsion devices, preservation devices, marinating devices, drain opener, fire extinguisher, lather-maker, pressurized cooking devices, nasal and sinus cleansing applications, humidifying device, nebualizing devices, atomizing devices, manicuring applications, massaging device, air delivering tool devices, and painting devices. However, it should also be appreciated that variation in construction may be necessary to achieve these alternative uses, which may include variations to compressed air source 16, compressed air line 18, slurry container 14, slurry mixture 26, spray tip member 36, hand piece 12, or small bore orifice 24.

It should be readily apparent that the present invention provide a number of useful advantages over the prior art, such as easily used as a home device due to the lack of a need for a pressurized water vessel. Additionally, the present invention is capable of varying the dilution of the slurry and consequently the level of abrasiveness or efficacy of the cleaning through the amount of water or other liquid used in wetting the dry components.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. An air appliance for dental prophylaxis comprising:

a compressed air source for supplying compressed air;

a hand piece in fluid communication with said compressed air source, said hand piece having a dental spray tip member configured for dental application to a patient's mouth, said hand piece having a compressed air delivery tube operable to receive said compressed air and deliver at least said compressed air to said dental spray tip member;

a component material container operable to contain a component material; and a component pathway defining fluid communication between said component material container and said dental spray tip member of said hand piece, said component pathway configured to deliver said component material to said dental spray tip member, said pathway comprising at least an upstream one-way valve and a downstream one-way valve disposed in series together forming at least one stage between said one-way valves, said at least one stage capturing at least a portion of said component material from said component material container during operation, said upstream one-way valve preventing flow of said component material within said at least one stage from flowing into said component material container, the component pathway is configured such that said component material and said compressed air are unmixed in the component pathway and are initially mixed outside of the distal spray tip member, the component pathway, and the delivery tube.

2. The air appliance according to claim 1 wherein said downstream one-way valve prevents flow of said component material within said at least one stage from flowing to said dental spray tip member until a predetermine internal pressure is achieved to overcome a biasing force of said downstream one-way valve.

3. The air appliance according to claim 1 wherein at least one of said one-way valves is a flapper valve.

4. The air appliance according to claim 1 wherein at least one of said one-way valves is made of a resilient material having a central aperture capable of opening in response to predetermined upstream pressure and automatically closing once said predetermined upstream pressure is removed.

5. The air appliance according to claim 1 wherein said component material container is adapted to be manually actuatable to urge said component material from said component material container past said upstream one-way valve to said at least one stage.

6. The air appliance according to claim 5 wherein said manual actuation is achievable via manual compression by an operator.

7. The air appliance according to claim 1 wherein said component material container is removably coupled directly to said hand piece.

8. The air appliance according to claim 1 wherein said component material container comprises threads and is threadedly engaged with said hand piece.

9. The air appliance according to claim 1 wherein said dental spray tip member is integrally formed with said hand piece.

10. The air appliance according to claim 1 wherein said dental spray tip member comprises an orifice, said orifice being made of a resilient material capable of enlarging in response to a clog or debris.

11. The air appliance according to claim 10 wherein said orifice is made of silicone.

12. The air appliance according to claim 10 wherein said orifice defines a diameter in the range of 0.020" and 0.045".

13. The air appliance according to claim 1, further comprising:
a light activation system operably associated with the hand piece, said light activation system having a lighting unit outputting light at a wavelength sufficient to activate said component material.

14. The air appliance according to claim 1 further comprising said component material, said component material is methylene blue dye.

15. The air appliance according to claim 1 further comprising said component material, said component material is a light activated medicament.

16. The air appliance according to claim 1 further comprising said component material being a mixture of dry abrasive and non-abrasive components that is capable of defining a slurry when a liquid is added.

17. The air appliance according to claim 1 further comprising said component material being chosen from the group consisting essentially of gel, cream, fluid, or colloid suspension form.

18. The air appliance according to claim 1 further comprising said component material being chosen from the group consisting essentially of an abrasive, a non-abrasive, an anionic surfactant, a cationic surfactant, a nonionic surfactant, a medicament, a flavoring, an astringent, a disinfectant, an oxygenating agent, an enzyme, a coenzyme, a vitamin, a mineral, an organic, an inorganic, a sweetener, a combatant, an antimicrobial, an antibiotic, a bacteria, a virus, an antiviral agent, a desensitizing agent, an odor-eating agent, an acid, a base, a neutral, a bleaching agent, an antioxidant, an anti-inflammatory agent, a sealant, a coating, an anti-tarter agent, an anti-adherent agent, an anti-agglomerate, a remineralization agent, a resorbable polymer, a copolymer, an astringent, a disinfectant, a time-releasing agent, a cox1 inhibitor, a cox2 inhibitor, a lipid, a protein, a carbohydrate, an oil alcohol, a phenol agent, a phosphorylated nucleotide, an amino acid, an antihistamine, a steroid, a disintegrin, a glycosaminoglycan, a growth factor, a periodontal tissue regenerator, an a hydrophobic layer.

19. An air appliance comprising:
a compressed air source for supplying compressed air;
a hand piece in fluid communication with said compressed air source, said hand piece having a spray tip member, said hand piece having a compressed air delivery tube operable to receive said compressed air and deliver at least said compressed air to said dental spray tip member along an air delivery tube;
a slurry container operable to contain a slurry; and
a slurry pathway defining fluid communication between said slurry container and said dental spray tip member of said hand piece, said slurry pathway configured to deliver said slurry to said dental spray tip member, said pathway comprising at least an upstream valve and a downstream valve disposed in series together forming at least one stage between said valves, said at least one stage capturing at least a portion of said slurry from said slurry container during operation, said upstream valve preventing flow of said slurry within said at least one stage from flowing into said slurry container, the slurry pathway is configured such that said slurry and said compressed air are unmixed in the component pathway and are initially mixed outside of the distal spray tip member, the component pathway, and the delivery tube.

* * * * *